United States Patent
Williams et al.

(10) Patent No.: US 9,987,159 B2
(45) Date of Patent: Jun. 5, 2018

(54) BACK SUPPORTER

(71) Applicants: Daniel Charles Williams, Barttlett, IL (US); Sarah Janie Williams, Bartlett, IL (US)

(72) Inventors: Daniel Charles Williams, Barttlett, IL (US); Sarah Janie Williams, Bartlett, IL (US)

( * ) Notice: Subject to any disclaimer, the term of this patent is extended or adjusted under 35 U.S.C. 154(b) by 685 days.

(21) Appl. No.: 14/469,330

(22) Filed: Aug. 26, 2014

(65) Prior Publication Data
US 2016/0058597 A1 Mar. 3, 2016

(51) Int. Cl.
*A61F 5/02* (2006.01)

(52) U.S. Cl.
CPC ............... *A61F 5/028* (2013.01); *A61F 5/02* (2013.01); *A61F 5/026* (2013.01)

(58) Field of Classification Search
CPC ..................................................... A61F 5/028
See application file for complete search history.

(56) References Cited

U.S. PATENT DOCUMENTS

| | | | | |
|---|---|---|---|---|
| 1,722,205 A * | 7/1929 | Freund | ............... | A61F 5/024 2/44 |
| 2,886,031 A * | 5/1959 | Robbins | ............... | A61F 5/024 602/19 |
| 5,224,924 A * | 7/1993 | Urso | ............... | A61F 5/024 135/71 |
| 5,405,313 A * | 4/1995 | Albin | ............... | A61F 5/026 602/19 |
| 5,462,518 A * | 10/1995 | Hatley | ............... | A61F 5/024 482/124 |
| 5,916,188 A * | 6/1999 | Ousdal | ............... | A61F 5/024 602/19 |
| 6,015,395 A * | 1/2000 | Kautzky | ............... | A61H 1/0229 602/19 |
| 7,200,870 B1 * | 4/2007 | Kolk | ............... | A41D 13/08 2/16 |
| 2011/0313337 A1 | 12/2011 | Goldfinch et al. | | |

* cited by examiner

*Primary Examiner* — Tarla Patel

(57) ABSTRACT

Disclosed herein are device embodiments for supporting a person's back. An embodiment comprises an adjustable belt and a pair of underarm supports attached to the sides of the belt. Each support comprises an underarm rest and a first spring, a second spring, and a third springs. Each support further comprises a first pin attached to the underarm rest, the first pin coupled to a top end of the first spring; a second pin coupled to a bottom end of the first spring and a top end of the second spring; and a third pin coupled to a bottom end of the second spring and a top end of the third spring. Each support further includes a base bottom coupled to a bottom end of the third spring and attached to the adjustable belt.

12 Claims, 5 Drawing Sheets

BACK SUPPORTER

BACKGROUND

Technical Field

Embodiments generally relate to support devices for the lower back.

Background

There are many back supporting devices which are known in the art. Some examples of similar types of devices are described in U.S. Pat. Nos. 5,405,313 and 6,015,395, and U.S. Pat. Application Publication No. 2011/0313337.

These devices are intended to provide relief to the lower back by reducing the load on the spine. Movement is typically reduced by the rigidity of these devices. This restriction makes it difficult to go through normal daily activities with reasonable comfort. Some devices even require surgically implanted hardware which brings along with it other risks.

Some back support devices are not intended to be used by a person while they are active, but only to be used during times at rest. Some devices are large and cumbersome, and discretion is not an option.

SUMMARY

The advantage of The Back Supporter is the freedom of movement and ability to go to work or do any other normal activity while wearing the device. The discretion of being worn under a loose fitting shirt without detection while removing pressure from the spine is a plus.

Disclosed herein are embodiments of a device for supporting a person's back. An embodiment comprises an adjustable belt and a pair of underarm supports attached to the sides of the belt. Each support comprises an underarm rest, a first spring, a second spring, and a third spring. Each support further comprises a first pin attached to the underarm rest, the first pin coupled to a top end of the first spring; a second pin coupled to a bottom end of the first spring and a top end of the second spring; and a third pin coupled to a bottom end of the second spring and a top end of the third spring. Each support further comprises a base bottom coupled to a bottom end of the third spring and to the adjustable belt.

DETAILED DESCRIPTION

Figure 1:
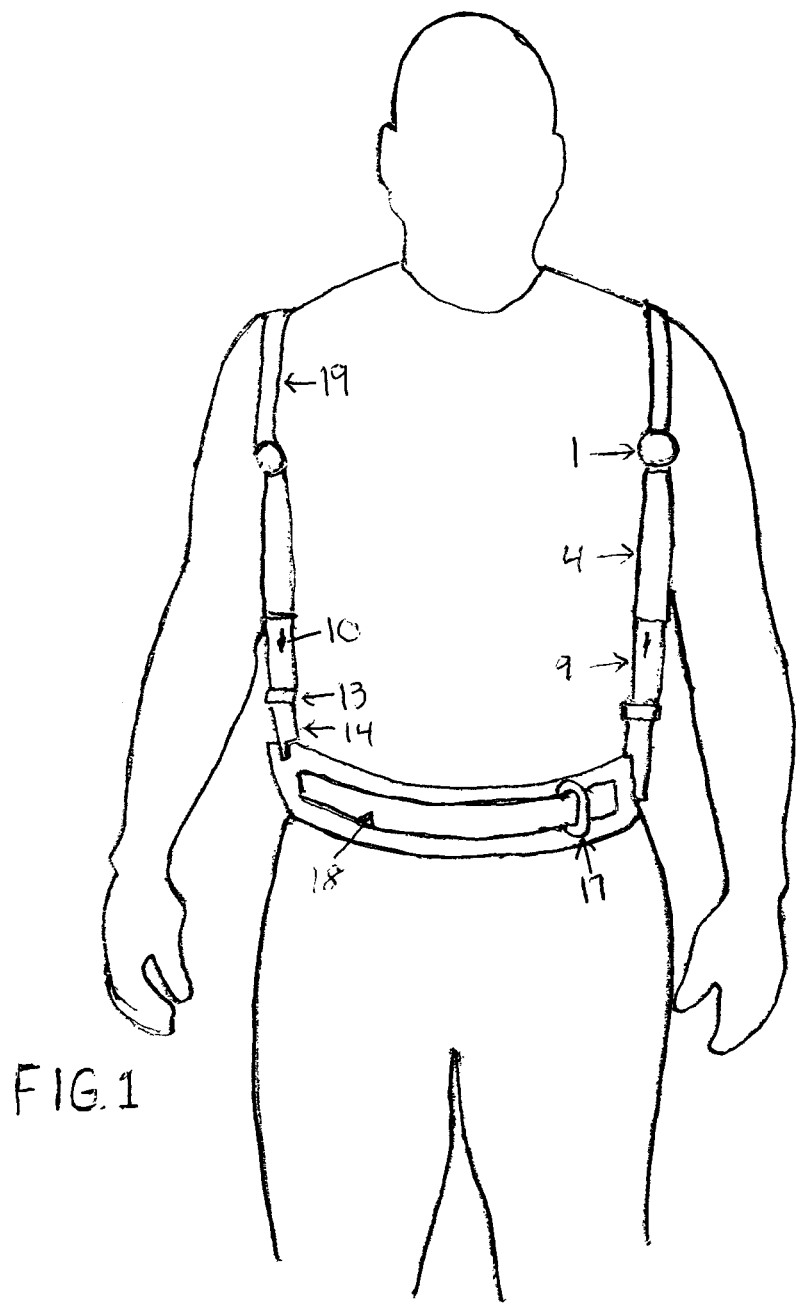
FIG. 1 illustrates a front view of the back supporter, according to an example embodiment.
Figure 2:
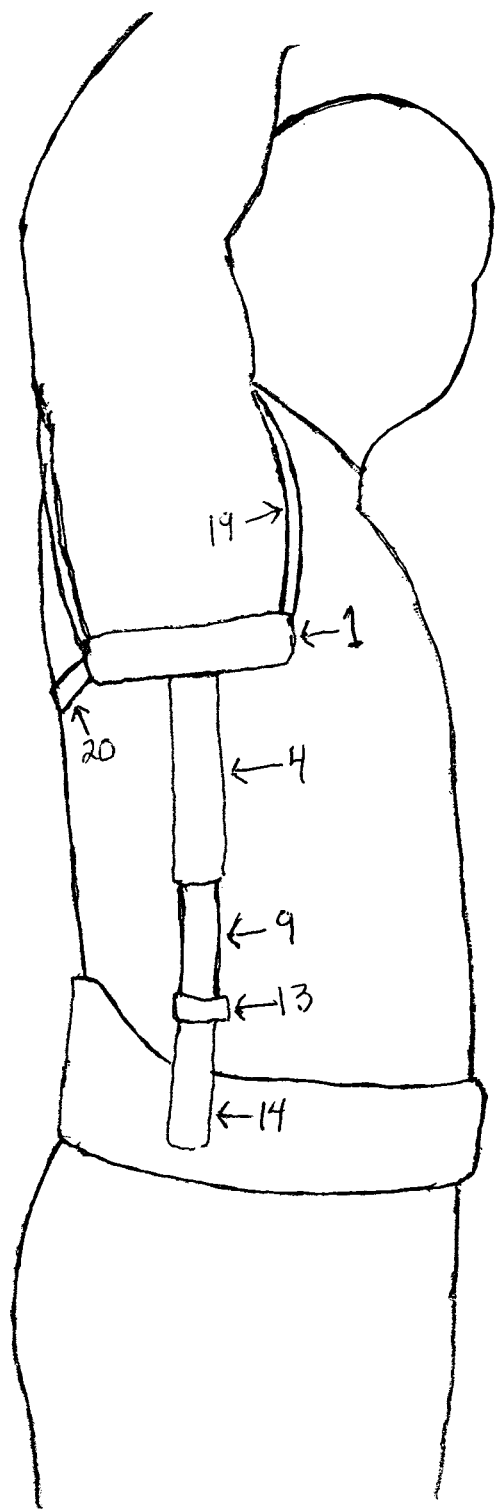
FIG. 2 illustrates a right side view of the back supporter, according to an example embodiment.
Figure 3:
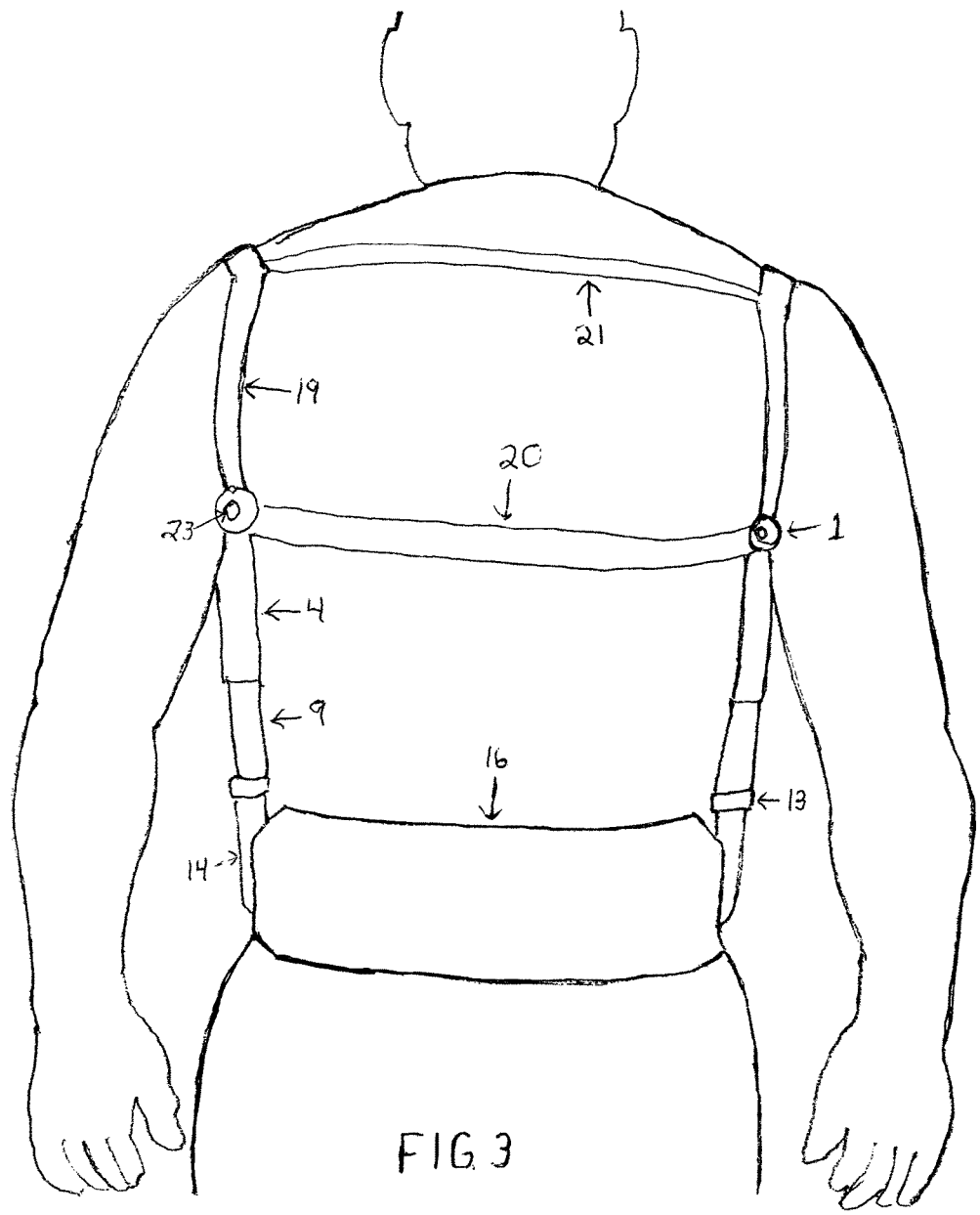
FIG. 3 illustrates a rear view of the back supporter, according to an example embodiment.
Figure 4:
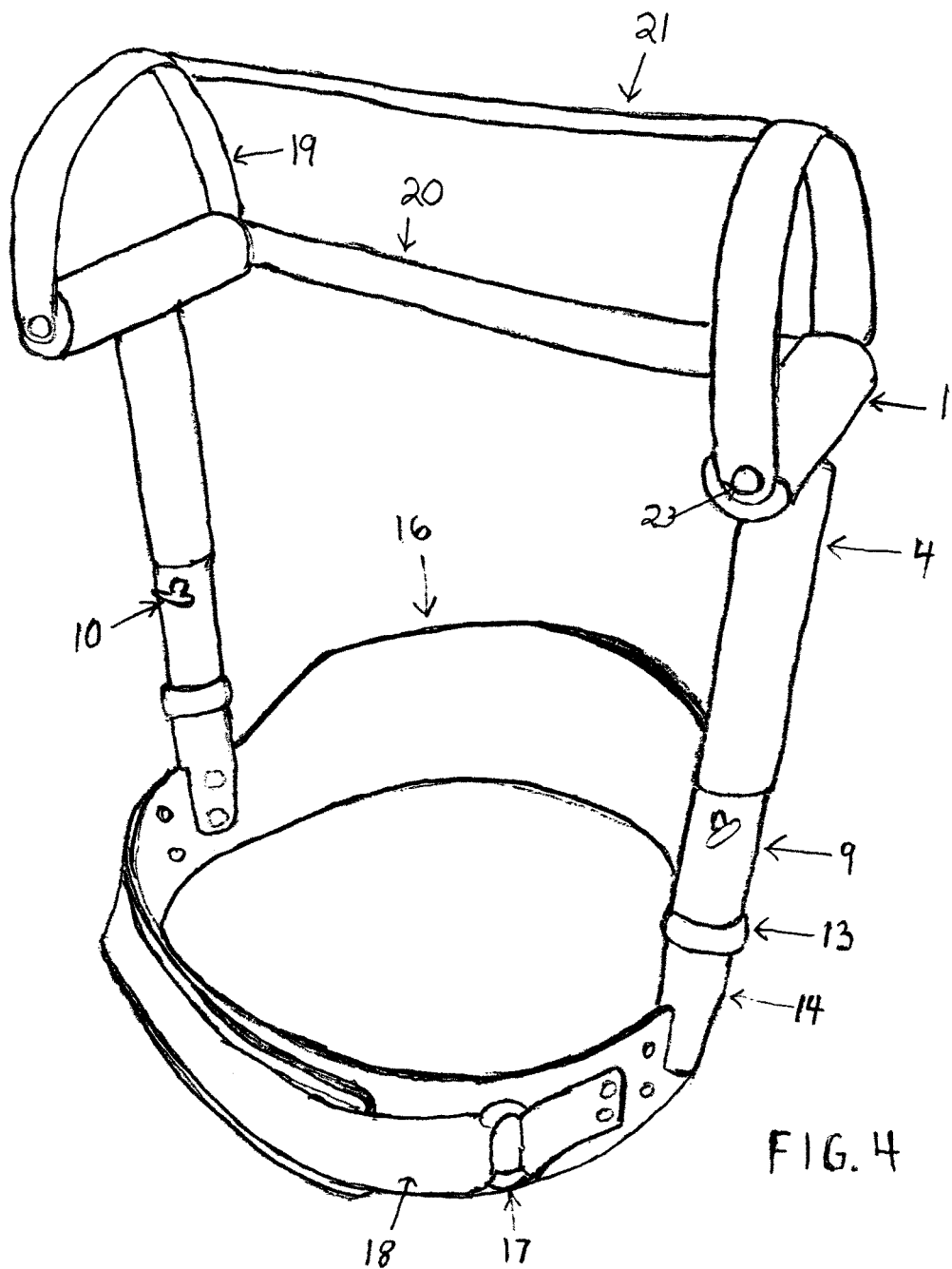
FIG. 4 illustrates a perspective view of the back supporter, according to an example embodiment.
Figure 5:
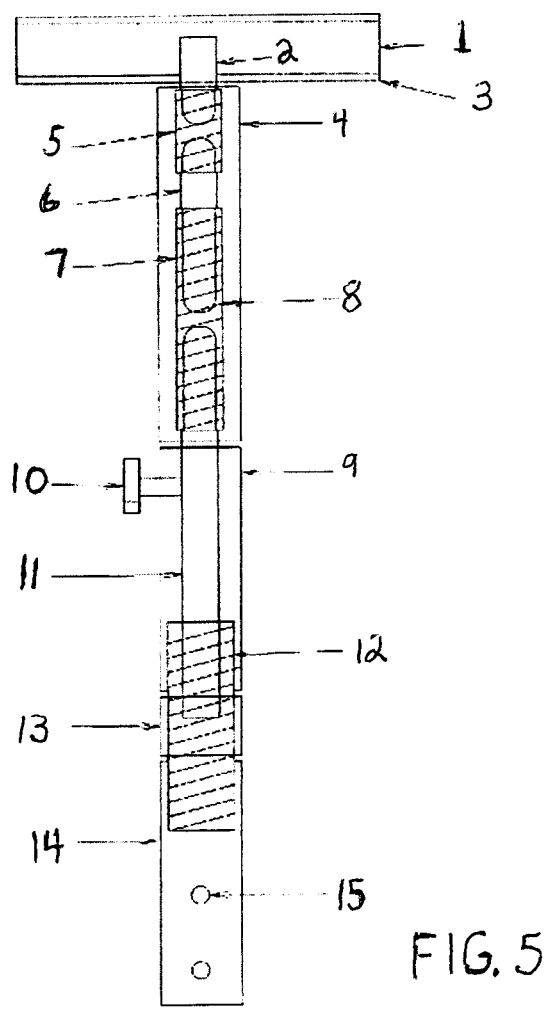
FIG. 5 illustrates a cross-section of an underarm support of the back supporter, according to an example embodiment.

Disclosed herein are embodiments of a device for supporting a person's back. FIG. 1 illustrates a front view of the back supporter. The back supporter closely fits the body of the user using an underarm support design and a belt. The belt includes a fabric hook and loop fastener (e.g., VELCRO®) that loops across the front of the belt for individualized fit. FIG. 2 illustrates the body's side profile wearing the pivoting underarm support along with the armrest fitting snugly under the armpit. FIG. 3 illustrates the high back of the belt for extra back support, along with elastic straps across the upper back to aid in keeping the arm supports in place while still allowing for flexibility in motion.

The back supporter is an improvement over other devices by using a set of spring loaded adjustable under arm supports comprised of a combination of pins and springs that are sturdy yet flexible. The three pin construction in the upper support when in the upright position work like they are one solid support. When the wearer bends the springs around the pins allow them to move with the wearer in any direction.

The pins may have a radius on top or bottom that allow them to move like ball joints against each other. The base is also a three piece unit with a spring between two halves that operate on the same principle as the top, full support in the upright position but flexibility to move forward or backward, and side to side. The base has a through hole that receives the upper support post. A thumb screw lock against this post allows adjustment up or down for the users height. Multiple holes are punched into the belt to allow horizontal adjustment for the wearer's most useful position for the underarm supports.

The belt is a six inch wide belt across the back tapered down to three inches wide in front. The belt is made of a durable five ply neoprene that gives more than sufficient support for the users back and for the side posts.

A back supporter may be specially designed with spring loaded adjustable underarm side supports for movement in any direction. The back supporter may be configured expressly to give lift to the torso, alleviate back pain by preventing compression of the spine and evenly distributing the weight of the upper body, via the brace's integrated spring loaded side support system, thus relieving pain and allowing for healing while still being able to move about.

The back supporter brace may be comprised of a wide 5ply neoprene belt that rests on the upper hip, with extra width in back for added support slightly contouring on the sides and front with a fabric hook and loop (e.g., VELCRO®) front fastener. The supporter may include a set of spring loaded adjustable side supports stemming from the upper sides of the belt straight up to the armpit of the user. Each side support may have thumb screws to adjust the length of the support, and may be fitted together with flexible springs and pins positioned to pivot with wearers movement. The supporter may have a plastic base that attaches to the sides to the belt and a set of foam rubber sleeves which cover the upper pins and springs. A set of underarm rests may be attached to the top of the spring loaded supports for the armpit to rest on and an elastic strap may be attached to the front and back end of each underarm rest over the shoulder. A set of elastic straps may be attached to the elastic underarm shoulder straps, one strap connected on each backend of the underarm rest and the other strap may be centered across the upper back connected to each shoulder strap.

The belt's front fastener may be an attached adjustable 2" fabric hook and loop fastener (e.g., VELCRO®) pull strap which feeds through a steel loop and folds back for individualized fastening fit. The springs may be compression springs designed to move in any direction with wearer. The base of the underarm side supports may be made of durable plastics (e.g., nylon plastics, NYLATRON®) and may have milled slots which attach firmly to the top of the belt with minimum exposure to the body. The base slot slide of the underarm support may be attached to the belt by two screws with adjustment positions forward or backward for adjustable side fit on the belt. The underarm spring loaded supports may have thumb screw locks which allow the underarm support to be readjusted up or down for vertical fit. The three pins in each support arm may be made of aluminum. The three pins in each support may be press fit into the compression springs.

The bottom pin of the underarm support fits into the base for the vertical adjustment may be approximately ½" in diameter with a flat milled on one side for the adjustment thumb screw to lock down on. The top of the pin may be turned down to fit the spring mounted on top of the pin. The center pin may be turned down to off fit the spring that is mounted on top of it and the top is turned down to fit the spring that is mounted on top of it. The top pin and the bottom pin may be turned down to fit the spring beneath. The top pin may be press fit ½" into the top arm rest.

Each arm support may be comprised of three compression springs designed to handle extreme amounts of downward pressure, but very little resistance to any lateral movement. The compression springs and pins may be covered with foam rubber sleeves. Each pin may have a radius on top or bottom that allow them to move like ball joints against each other.

A hip belt (16) designed to rest on the upper hip, approx. 6" wide in the back and tapered down to 3" wide on sides and in front, made of 5ply neoprene material. This belt is worn to be snugly around the user's waist. The belt (16) has an attached 1½" pull strap (18) that is fed through a ¼" steel loop (17) and fastens in place by heavy duty Velcro. There are a pair of underarm supports attached to the sides of the belt (16) by way of the base bottoms (14). The side supports are spring loaded (5,7,12) and are held in place by pins (2,6,11). Foam rubber sleeves (3,4,13) and the top base (9) cover the springs (5,7,12) pins (2,6,11) and underarm rest (1). Underarm rests (1) are attached to the top of the underarm side supports by the top pins (2). Elastic shoulder straps (19) are attached to the front and back side of the underarm rests with a screw (23) to which the arm is fed through and the straps rest on top of the shoulder. The thumb screws (10) located in the center front of the underarm support on the top base (9) allows the vertical position of the underarm support to adjust for height. In back of the device are upper and lower elastic straps (20, 21) which aid in holding the underarm support in place.

What is claimed is:

1. A body support device comprising:
   an adjustable belt;
   a pair of underarm supports attached to the sides of the belt, each support comprising:
   an underarm rest;
   a first spring, a second spring, and a third spring;
   a first pin attached to the underarm rest, the first pin coupled to a top end of the first spring;
   a second pin coupled to a bottom end of the first spring and a top end of the second spring; and
   a third pin coupled to a bottom end of the second spring and a top end of the third spring, and
   a base bottom coupled to a bottom end of the third spring and attached to the adjustable belt; wherein the first, second and third pins have a rounded top or bottom that allows ball joint movement against each other and wherein each of first, second and third pins is press fit into its corresponding end of the first, second and third springs.

2. The device of claim 1, wherein each of the first, second and third springs are compression springs.

3. The device of claim 1, wherein the base bottom is comprised of a plastic material with milled slots that couple the base bottom to the adjustable belt.

4. The device of claim 3, wherein each side of the adjustable belt further comprises a plurality positions for attaching each base bottom to the adjustable belt and adjusting a side fit on the adjustable belt.

5. The device of claim 1, wherein the adjustable belt comprises a pull strap and a loop for feeding the pull strap.

6. The device of claim 1, wherein the adjustable belt further comprises fabric hook and loop fasteners for fastening the pull strap to the adjustable belt.

7. The device of claim 1, wherein each of the pair of underarm supports further comprises one or more foam rubber sleeves covering the first, second, and third springs.

8. The device of claim 1, wherein each of the pair of underarm supports further comprises a rubber sleeve covering the underarm rest.

9. The device of claim 1, wherein each of the pair of underarm supports further comprises an elastic shoulder strap attached to a front and back side of the underarm rest.

10. The device of claim 1, wherein each of the pair of underarm supports further comprises a thumb screw for adjusting the vertical position of the underarm support.

11. The device of claim 1, further comprising one or more elastic straps connecting the pair of underarm supports on the back of the device.

12. The device of claim 1, wherein each of the first, second, and third pins is comprised of aluminum.

* * * * *